United States Patent [19]

DePasquale et al.

[11] 4,408,048

[45] Oct. 4, 1983

[54] PROCESS FOR MAKING 5-FLUOROURACIL

[75] Inventors: Ralph J. DePasquale, Gainesville; Paul D. Schuman, Hawthorne, both of Fla.

[73] Assignee: PCR Incorporated, Gainesville, Fla.

[21] Appl. No.: 264,714

[22] Filed: May 18, 1981

Related U.S. Application Data

[62] Division of Ser. No. 110,192, Jan. 7, 1980, Pat. No. 4,299,961.

[51] Int. Cl.$^3$ .............................................. C07D 239/20
[52] U.S. Cl. ..................................... 544/313; 424/251
[58] Field of Search ........................... 544/313; 424/251

[56] References Cited

U.S. PATENT DOCUMENTS

| | | | |
|---|---|---|---|
| 3,682,917 | 8/1972 | Knuniants et al. | 544/313 |
| 4,122,251 | 10/1978 | Misaki et al. | 544/313 |
| 4,186,266 | 1/1980 | Yamazaki et al. | 544/313 |

OTHER PUBLICATIONS

Brown, The Pyrimidines, pp. 148–149 (1970) (Wiley-Interscience).

*Primary Examiner*—Nicholas S. Rizzo
*Attorney, Agent, or Firm*—Murray & Whisenhunt

[57] ABSTRACT

A process for preparing 5-fluorouracil, and a novel starting compound for such process, are disclosed. The novel starting compound is 2,4,5-trifluoropyrimidine. The process comprises hydrolyzing the 2,4,5-trifluoropyrimidine at a temperature of about 2° to about 100° C., thereby directly producing the compound 5-fluorouracil.

5-Fluorouracil is a known anti-tumor agent, which has been used in the treatment of various types of cancers. In addition, 5-fluorouracil is a starting material for the production of certain types of pro-drugs, which are metabolized to form 5-fluorouracil in the body, such as, for instance, the compound 1-(2-tetrahydrofuryl)-5-fluorouracil.

8 Claims, No Drawings

PROCESS FOR MAKING 5-FLUOROURACIL

This is a divisional application of Ser. No. 110,192, filed Jan. 7, 1980, now U.S. Pat. No. 4,299,961.

BACKGROUND OF THE INVENTION

The present invention is directed to a process for preparing 5-flourouracil, and to a novel starting compound, 2,4,5-trifluoropyrimidine, used in the process.

U.S. Pat. Nos. 3,280,124 and 3,314,955 disclose that 2,4,6-trifluoropyrimidine can be obtained by reacting 2,4,6-trichloropyrimidine with anhydrous potassium fluoride at elevated temperatures, to provide the desired 2,4,6-trifluoropyrimidine in high yield with excellent purity.

U.S. Pat. No. 3,964,444 teaches, at column 2, lines 30–33, that chlorine or bromine substituents in the 5- position of the pyrimidine ring are exchanged for a fluorine substituent only with difficulty, or not at all. The patent deals with a process for exchanging fluorine for chlorine or bromine substituents in compounds such as 2,4,5,6-tetrachloro- or bromopyrimidine, or 2,4,6-trichloro- or bromo-pyrimidine, by action of anhydrous hydrofluoric acid under mild conditions. The art would not expect the 5- position halogen atom to be involved in an exchange reaction with fluorine.

U.S. Pat. No. 2,937,171 discloses 2,4,5-tribromopyrimidine as a starting compound (Example XV), which is reacted with $SF_4$ to exchange fluorine for halogen. The patentee indicates that the mechanism of the reaction is not exactly known, but that at least one chlorine or bromine atom is displaced with fluorine (note column 3, lines 8–19). However, U.S. Pat. No. 3,280,124 discussed above discloses, at column 1, lines 20–26, that when an attempt was made to flourinate 2,4,6-trichloropyrimidine by means of sulfur tetrafluoride, only mixtures of partly fluorinated pyrimidines were obtained. This would suggest that only partially fluorinated compounds would be obtained in an attempt to react 2,4,5-tribromopyrimidine with sulfur tetrafluoride, especially in view of the well-known difficulty of displacing halogen substituents at the 5- position, as borne out by U.S. Pat. No. 3,694,444 at column 2, lines 30 et seq.

M. J. Langerman and C. K. Banks, J. Am. Chem. Soc., 73, 3011 (1951) relates to preparing 2,4,6-trisubstituted pyrimidines, and has no disclosure of any compounds having a substituent in the 5- position.

H. Schroeder, E. Kober, H. Ulrich, R. Ratz, H. Agahigian and C. Grundman, J. Org. Chem. 27, 2580 (1952) discloses attempts to convert tetrachloropyrimidine into tetrafluoropyrimidine, with all attempts to replace the chlorine atom in the 5- position with fluorine being a failure. The product produced by reaction of tetrachloropyrimidine with silver flouride was 5-chloro-2,4,6-trifluoropyrimidine. Tetrafluoropyrimidine was finally obtained by reacting 2,4,6-trichloropyrimidine with silver fluoride to produce 2,4,6-trifluoropyrimidine, which was in turn reacted with silver difluoride to form the desired tetrafluoropyrimidine. As is clear from the results reported by Schroeder et al, the displacement of the halogen in the 5- position by fluorine is most difficult.

R. E. Banks, D. S. Field and R. H. Haszeldine, J. Chem. Soc. (C), 1822 (1967) discusses the results of nucleophilic attack upon tetrafluoropyrimidine. Banks et al indicate, in the second paragraph of the article, that the fluorine substituent in the 5- position resists displacement from tetrafluoropyrimidine. The only aqueous hydrolysis step disclosed in the Banks reaction schemes, set forth on page 1823 of the article, is reaction (i), which displaces fluorine with a hydroxyl radical at the 4- position. Other reactions relate to the displacement of fluorine atoms by a methoxy group, with the methoxy group displacing, in order, the fluorine substituents in the 4- position, the 6- position, and the 2- position, with no apparent attack at the 5- position. Those in the art would not be able to gauge the effect on the activity of the 5- position in compounds lacking the 6- position fluorine atom. For instance, the difference in behavior between the trichloropyrimidine and the tetrachloropyrimidine of the Schroeder et al article, discussed above, serves to further illustrate the unpredictability of the trifluorinated product.

U.S. Pat. No. 4,140,857 discloses a process for preparing 2,4,5-trichloropyrimidine by reacting N,N'-bis-(2-cyanoethyl)-thioperoxy dicarboxylic acid diamides with chlorine at temperatures of from 0° to 40° C. The reaction mixture is then subsequently heated in the absence of chlorine to temperatures of 100° to 150° C. to form the desired compound.

SUMMARY OF THE INVENTION 5-fluorouracil is prepared by hydrolyzing 2,4,5-trifluoropyrimidine at a temperature of about 2° to about 100° C., to produce the desired 5-fluorouracil product. The 2,4,5-trifluoropyrimidine is in turn produced by reacting a compound of the formula

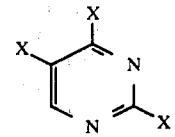

wherein each X is Cl or Br with a metal fluoride at a temperature of about 20° to about 500° C.

The 2,4,5-trifluoropyrimidine is a novel product, and comprises part of the present invention.

DETAILED DESCRIPTION OF THE INVENTION

It is known that in the pyrimidine ring system substituents which are recognized for their leaving group ability are displaced by nucleophilic attack, and/or by bases when their original attachment site is at the 2, 4, or 6 position. In comparison, such leaving groups are only displaced with difficulty when attached to the 5- position. Note Langerman et al., supra; Schroeder et al., supra; Banks et al, supra; and W. R. Boon, W. G. M. Jones and G. R. Ramage, J. Chem. Soc., 99 (1951).

5-fluorouracil is prepared according to the present invention by first preparing 2,4,5-trihalopyrimidines and subsequently converting these intermediate products into the compound 2,4,5-trifluoropyrimidine, which upon hydrolysis yields 5-fluorouracil. The overall reaction scheme may be illustrated below:

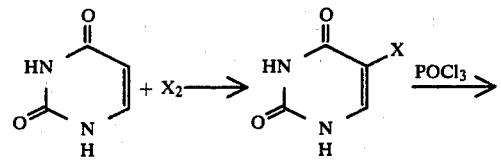

-continued

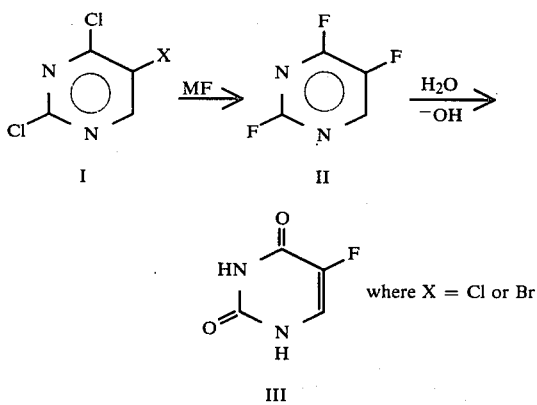

where X = Cl or Br

It is greatly preferred for the substituent X on the pyrimidine ring to be bromine or chlorine, but it is possible that other known leaving groups, such as, for instance, $NO_2$, $N_2^+$, $OSO_2Ar$ would also be suitable. The metal or metaloid fluoride used for the conversion of compounds I to compounds II can either be a Lewis acid or base, or combination of the two, and is generally chosen from the class of reagents useful for fluoride-leaving group metathesis reactions. Suitable materials include $AgF$, $HgF_2$, $CoF_3$, $HF$, and the like. The working temperature for the conversion of compounds I to compounds II is in the range of 25° to 550° C., and is preferably from 250° to 450° C. Metal fluorides are preferably a fluoride of a metal of groups IA, VIII, Ib or IIB of the Mendeleef Periodic Table.

The hydrolysis reaction to convert compounds II to compound III, that is, 5-fluorouracil, can be readily accomplished using conventional hydrolysis techniques. The hydrolysis can be accomplished by the addition of at least 2 moles of water per mole of 2,4,5-trifluoropyrimidine, at a temperature within the aforesaid range. Such simple aqueous hydrolysis generally proceeds relatively slowly, and it is preferred that the hydrolysis be conducted under reflux conditions. The hydrolysis can be conducted using an inert water stable cosolvent, such as tetrahydrofuran (THF), dioxane, DMF, acetone, or the like. The use of such a cosolvent increases the contact between the water and 2,4,5-trifluoropyrimidine, and results in increased reaction rates.

Preferably, however, the reaction is conducted in the presence of a hydrolysis catalyst, and especially a basic hydrolysis catalyst, such as an alkali hydroxide, and especially sodium hydroxide or potassium hydroxide. At least two equivalents of the basic catalyst should be used, that is, at least two moles of basic catalyst per mole of trifluoropyrimidine, as the catalyst will be consumed in the reaction. Normally the basic catalyst will be used with the reaction mixture at a pH of greater than 7, and the initial pH of the reaction mixture can be as high as 14, although normally the pH will be no greater than 12 or so.

The above-mentioned temperature range of 2° to 100° C. is preferred, but it is to be understood that with the use of an inert water-soluble cosolvent, the freezing point of the reaction mixture may be lowered to the point that temperatures less than 2° C. could be utilized, but it is to be understood that such reduced temperatures will result in a slower hydrolysis reaction rate. The use of elevated pressures and therefore elevated temperatures, above the aforesaid range, is also possible. Elevated pressures of up to 500 psi can be used if desired, with the hydrolysis temperature as high as 150° C. or so, to result in faster hydrolysis reaction times, but normally such elevated pressure/temperature conditions are unnecessary for acceptable reaction rates, and add to the cost of the reaction, so this approach is not preferred.

At least two moles of water per mole of 2,4,5-trifluoropyrimidine will be used, and preferably an excess of water will be utilized. The 5-fluorouracil product is soluble to the extent of about 1% at room temperature and pH 7 in water, and is normally removed from the reaction mixture by a filtration step. For this reason, it is preferred that no great excess of water be utilized, as the amount of unrecovered 5-fluorouracil would then increase, but there is no other reason why a great excess of water could not be used if desired.

While the above discussion is with relation to the direct aqueous hydrolysis of 2,4,5-trifluoropyrimidine, it is to be understood that indirect methods can be used to convert the 2,4-fluorine substituents to hydroxyl groups. For instance, an alcoholic hydrolysis or alcoholysis reaction could be utilized to form alkoxy groups of 1 to 6 carbon atoms each at the 2- and 4- positions of the pyrimidine ring. The alkoxy groups could then be cleaved in a further reaction step, as is conventional in the art, to replace the 1 to 6 carbon atom alkoxy groups with hydroxyl groups, thereby producing the desired hydroxyl groups. Such multi-step conversions are generally more extensive, and require greater work-up of the final product, as leading to additional, unwanted by-products, so normally will not be used.

EXAMPLES OF THE INVENTION

EXAMPLE A

Preparation of 5-chlorouracil and 5-bromouracil

Uracil was chlorinated and brominated by the procedures described in T. B. Johnson and J. Spraque, J. Am. Chem. Soc., 59 2436 (1937); S. Y. Wang, Jr. Org. Chem. 24, 11 (1954) to afford 5-chlorouracil and 5-bromouracil, respectively.

EXAMPLE B

Preparation of 5-bromo-2,4-dichloropyrimidine 5-bromouracil (30 g, 0.16 mole) was added to a flask containing 130 ml of $POCl_3$. The mixture was heated at reflux for 4 days. During this time the reaction contents were protected from atmospheric moisture; HCl gas was evolved and the solution became homogeneous. Excess $POCl_3$ was removed by distillation at atmospheric pressure. Continued distillation at reduced pressure afforded the title compound, bp 85°–90°/4 mm (29.7 g, 82% yield).

Anal. Calcd for $C_4HBrCl_2N_2$ C 21.05, H 0.44, N 12.3
Found C, 21.35, H, 0.92, N, 12.3

EXAMPLE C

Preparation of 2,4,5-Trichloropyrimidine

By using a procedure similar to the above the titled compound was prepared from 5-chlorouracil and phosphorous oxychloride in 76% yield, bp 50°/1 mm.

Anal. calcd for $C_4HCl_3N_2$ C, 25.97, H, 0.58, N, 15.4
Found C, 26.15, H, 0.54, N, 15.3

EXAMPLE 1

Preparation of 5-fluorouracil 2,4,5-trichloropyrimidine (1.0 g) and anhydrous potassium fluoride (3.3 g) was charged into a 10 ml stainless steel reactor in vacuuo and heated to 300° for 24 hours. The vessel is cooled to 150° and at this temperature the volatiles are transferred into a trap in vacuuo. There was collected 0.5 g of a mixture of tri-chloro-fluoropyrimidines. Water, (10 ml) was added to this condensate and the solution was made basic with aqueous NaOH and heated at 80° for 4 hours. TLC of this solution (multiple development with ethyl acetate, acetone, water in a 70:40:10 ratio and visualized by ultraviolet) showed three components in a 5:4:1 ratio shown to be 5-chlorouracil, 5-fluorouracil, and uracil, respectively by comparison to authentic samples.

EXAMPLE 2

Example 1 was repeated, substituting anhydrous sodium fluoride for the potassium fluoride. There was obtained 0.7 g of trihalopyrimidines, hydrolysis of which resulted in an 8:1 ratio of 5-chlorouracil to 5-fluorouracil, with a trace of uracil detected.

EXAMPLE 3

Example 1 was repeated, using 5-bromo-2,4-dichloropyrimidine (1.0 g) in place of the 2,4,5-trichloropyrimidine. After work-up, 0.3 g of the trihalopyrimidine mixture was obtained, which after hydrolysis yielded 5-bromouracil:uracil:5-fluorouracil in a 6:3:1 ratio, respectively.

EXAMPLE 4

Example 1 was repeated, using 5-bromo-2,4-dichloropyrimidine (1.0 g) and anhydrous antimony trifluoride (3.3 g) to produce 0.3 g of liquid mixed trihalopyrimidine, which after hydrolysis yielded 5-bromouracil:5-fluorouracil:uracil in a ratio of 4:1:trace, respectively.

EXAMPLE 5

Preparation of 2,4,5-Trifluoropyrimidine

A dry, cylindrical (18×2.5×0.25") mild steel reactor was fitted with a bursting disc (1,000 psi), pressure gauge and venting system. The reactor was charged with a premixed sample of potassium fluoride (anhydrous, 320 g, 5.5 moles) and 2,4,5-trichloropyrimidine (95 g, 0.52 mole). The reaction was wrapped with heating coils and heated at 400°±25°/22 hr. During that time the pressure reached a maximum of 350 psig. The reactor was cooled and the contents vented at reduced pressure. There was collected 24.0 g of a colorless liquid. This material was found to consist predominantly of the titled compound accompanied by minor amounts of mixed chlorodifluoropyrimidines. The titled compound, bp 99°, was purified by distillation.

The $^{19}F$ NMR spectrum of 2,4,5-trifluoropyrimidine neat, relative to external trifluoroacetic acid, shows $F_2$ at 48.5 ppm (D, 1) $F_4$ at 56.9 ppm (D,1) and $F_5$ at 173.3 ppm (m, 1 ) while the $^1H$ NMR shows a multiplet at 8.33 ppm. The mass spectrum showed a parent ion at m/e 134; other prominent ions were observed at m/e 115, 107, 89, 70, 62, 58, and 51.

What is claimed is:

1. Process for preparing 5-fluorouracil comprising hydrolyzing 2,4,5-trifluoropyrimidine at a temperature of about 2° to about 100° C. to produce 5-fluorouracil.

2. Process of claim 1, wherein said process is conducted in the presence of a catalytic amount of a hydrolysis catalyst.

3. Process of claim 1, wherein the hydrolysis is accomplished by the addition of at least 2 moles of water per mole of said 2,4,5-trifluoropyrimidine.

4. Process of claim 3, wherein said hydrolysis is conducted under reflux conditions.

5. Process of claim 3, herein said hydrolysis is conducted using an inert water-stable cosolvent to increase the contact between said water and said 2,4,5-trifluoropyrimidine.

6. Process of claim 3, wherein said reaction is conducted in the presence of a hydrolysis catalyst.

7. Process of claim 6, wherein said hydrolysis catalyst is a basic hydrolysis catalyst.

8. Process of claim 7, wherein at least 2 moles of said basic hydrolysis catalyst are used per mole of said 2,4,5-trifluoropyrimidine.

* * * * *